(12) United States Patent
Takemoto et al.

(10) Patent No.: US 9,913,641 B2
(45) Date of Patent: Mar. 13, 2018

(54) SURGICAL INSTRUMENT AND TISSUE DISSECTING UNIT

(71) Applicant: OLYMPUS CORPORATION, Hachioji-shi, Tokyo (JP)

(72) Inventors: Shotaro Takemoto, Tokyo (JP); Kunihide Kaji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/368,072

(22) Filed: Dec. 2, 2016

(65) Prior Publication Data

US 2017/0079645 A1    Mar. 23, 2017

Related U.S. Application Data

(63) Continuation of application No. PCT/JP2015/064309, filed on May 19, 2015.

(30) Foreign Application Priority Data

Aug. 4, 2014   (JP) .................................. 2014-158526

(51) Int. Cl.
*A61B 17/068* (2006.01)
*A61B 17/072* (2006.01)
(Continued)

(52) U.S. Cl.
CPC ........ *A61B 17/0682* (2013.01); *A61B 17/072* (2013.01); *A61B 17/07207* (2013.01);
(Continued)

(58) Field of Classification Search
CPC ........... A61B 2017/07285; A61B 2017/08278; A61B 2017/00367; A61B 2017/07221; A61B 17/072; A61B 17/07207
See application file for complete search history.

(56) References Cited

U.S. PATENT DOCUMENTS 5,389,098 A * 2/1995 Tsuruta ............ A61B 17/00234
606/142
7,434,717 B2 * 10/2008 Shelton, IV ......... A61B 17/105
227/175.1
(Continued)

FOREIGN PATENT DOCUMENTS

JP   H08-289895 A   11/1996
JP   2009-034487 A   2/2009
(Continued)

OTHER PUBLICATIONS

Aug. 18, 2015 International Search Report issued in International Patent Application No. PCT/JP2015/064309.

*Primary Examiner* — Andrew M Tecco
(74) *Attorney, Agent, or Firm* — Oliff PLC

(57) ABSTRACT

A surgical instrument includes an insertion section, a first jaw and a second jaw provided at a distal end portion of the insertion section, having predetermined curved shapes and configured to grasp tissue; a guide section formed along the predetermined curved shape and disposed in at least one of the first jaw and the second jaw; an actuation section which is movable by being guided by the guide section; a shaft body provided at the actuation section and configured to be rotatable about a rotation axis parallel to a center line of the shaft body; and a blade section connected to the shaft body at a position apart from the rotation axis in a direction across to the shaft body and configured to be directed to the shaft body, the blade section being rotatable about the rotation axis.

10 Claims, 10 Drawing Sheets

(51) Int. Cl.
*A61B 17/00* (2006.01)
*A61B 17/29* (2006.01)

(52) U.S. Cl.
CPC .............. *A61B 2017/00367* (2013.01); *A61B 2017/07221* (2013.01); *A61B 2017/07228* (2013.01); *A61B 2017/07278* (2013.01); *A61B 2017/07285* (2013.01); *A61B 2017/2905* (2013.01); *A61B 2017/2937* (2013.01)

(56) References Cited

U.S. PATENT DOCUMENTS

| | | | | |
|---|---|---|---|---|
| 8,348,124 B2* | 1/2013 | Scirica | ............. | A61B 17/07207 227/175.1 |
| 8,628,544 B2* | 1/2014 | Farascioni | ....... | A61B 17/07207 227/175.1 |
| 8,657,177 B2* | 2/2014 | Scirica | ............. | A61B 17/07207 227/176.1 |
| 9,386,985 B2* | 7/2016 | Koch, Jr. | ......... | A61B 17/07207 |
| 2007/0213743 A1* | 9/2007 | McGuckin, Jr. | . | A61B 17/00234 606/139 |
| 2008/0169327 A1* | 7/2008 | Shelton | ................ | A61B 17/105 227/176.1 |
| 2008/0308601 A1* | 12/2008 | Timm | .............. | A61B 17/07207 227/175.1 |
| 2009/0039137 A1* | 2/2009 | Viola | ............... | A61B 17/07207 227/176.1 |
| 2010/0076459 A1* | 3/2010 | Farascioni | ........ | A61B 17/07207 606/143 |
| 2010/0252611 A1* | 10/2010 | Ezzat | ................... | A61B 17/072 227/180.1 |
| 2010/0320252 A1* | 12/2010 | Viola | ............... | A61B 17/07207 227/176.1 |
| 2012/0199628 A1* | 8/2012 | Scirica | ............. | A61B 17/07207 227/175.1 |
| 2013/0098969 A1* | 4/2013 | Scirica | ............. | A61B 17/07207 227/180.1 |
| 2013/0105545 A1* | 5/2013 | Burbank | .............. | A61B 17/068 227/175.1 |
| 2014/0103093 A1* | 4/2014 | Koch, Jr. | ......... | A61B 17/07207 227/180.1 |

FOREIGN PATENT DOCUMENTS

| | | |
|---|---|---|
| JP | 2013-051977 A | 3/2013 |
| JP | 2013-542004 A | 11/2013 |
| WO | 96/18344 A2 | 6/1996 |
| WO | 2012/044848 A1 | 4/2012 |

* cited by examiner

SURGICAL INSTRUMENT AND TISSUE DISSECTING UNIT

The application is a continuation application based on PCT Patent Application No. PCT/JP2015/064,309, filed May 19, 2015, claiming priority based on Japanese Patent Application No. 2014-158526, filed Aug. 4, 2014, the contents of which are incorporated herein by reference.

FIELD OF THE INVENTION

The present invention relates to a surgical instrument and a tissue dissecting unit.

DESCRIPTION OF RELATED ART

In the related art, a tool configured to simultaneously perform suture and dissection of living body tissue is known.

For example, in Published Japanese Translation No. 2013-542004 of PCT International Publication and Japanese Unexamined Patent Application, First Publication No. H08-289895, surgical instruments including a cartridge in which a plurality of staples are accommodated, a blade section configured to dissect living body tissue, and a manipulation unit for dissecting the tissue using the blade section and shooting staples into the tissue are disclosed.

In addition, in Japanese Unexamined Patent Application, First Publication No. H08-289895, a surgical instrument capable of moving a blade section along a cartridge having a curved shape is disclosed.

SUMMARY OF THE INVENTION

A surgical instrument according to a first aspect of the present invention includes an insertion section configured to be inserted into a body; a first jaw and a second jaw provided at a distal end portion of the insertion section, the first jaw and the second jaw having predetermined curved shapes and configured to grasp tissue; a guide section formed along the predetermined curved shape and disposed in at least one of the first jaw and the second jaw; an actuation section which is movable by being guided by the guide section; a shaft body provided at the actuation section and in which a center line of the shaft body extends from the first jaw toward the second jaw, the shaft body configured to be rotatable about a rotation axis parallel to the center line; and a blade section connected to the shaft body at a position apart from the rotation axis in a direction across to the shaft body and configured to be directed to the shaft body, the blade section being rotatable about the rotation axis.

According to a second aspect of the present invention, the surgical instrument according to the first aspect may further include a wire extending from a proximal end portion to a distal end portion of the guide section, being returned at the distal end portion of the guide section to extend toward the proximal end portion of the guide section, and being connected to the actuation section.

According to a third aspect of the present invention, the surgical instrument according to the second aspect may further include a suture unit configured to suture the tissue grasped by the first jaw and the second jaw.

According to a fourth aspect of the present invention, in the surgical instrument according to the second aspect, the actuation section may have a guided section having a disk-shape, the guided section being engaged with the guide section and in which the wire is wound on an outer periphery of the guided section, and the shaft body is fixed to the guided section such that the centerline of the shaft body passes through a center of the guided section.

According to a fifth aspect of the present invention, in the surgical instrument according to the fourth aspect, the guided section may have a sliding surface which forms a curved surface shape protruding toward the shaft body at a surface to which the shaft body is fixed among outer surfaces of the guided section, the sliding surface which comes in point contact with the guide section.

According to a sixth aspect of the present invention, in the surgical instrument according to the second aspect, the blade section may be inclined with respect to the centerline of the shaft body.

According to a seventh aspect of the present invention, in the surgical instrument according to the second aspect, the actuation section may have a guided section formed in a disk-shape, the guided section being engaged with the guide section and in which the wire is wound on an outer periphery of the guided section, and the shaft body may be fixed to the guided section such that the centerline of the shaft body extends in parallel to a centerline of the guided section at a position spaced apart from a center of the guided section.

According to a eighth aspect of the present invention, in the surgical instrument according to the second aspect, the actuation section may have a guided section formed in a disk-shape, the guided section being engaged with the guide section and in which the wire is wound on an outer periphery of the guided section, and the shaft body may be connected to the guided section such that the centerline of the shaft body passes through a center of the guided section and the shaft body is rotatable with respect to the guided section.

According to a nineth aspect of the present invention, in the surgical instrument according to the second aspect, the actuation section may have a stopper structure which is capable of abutting the guide section to restrict that the shaft body rotates 180° or more with respect to the guide section.

A tissue dissecting unit according to a tenth aspect of the present invention includes: an actuation section which is movable along a predetermined curved shape of a jaw having the predetermined curved shape; a shaft body provided at the actuation section; and a blade section connected to the shaft body, wherein the shaft body and the blade section are rotatable about a rotation axis parallel to a center line of the shaft body, and the blade section is disposed at a position apart from the rotation axis in a direction across to the shaft body, and connected to the shaft body so as to be directed to the shaft body.

DETAILED DESCRIPTION OF THE PREFERRED EMBODIMENTS (First Embodiment)

Figure 1:
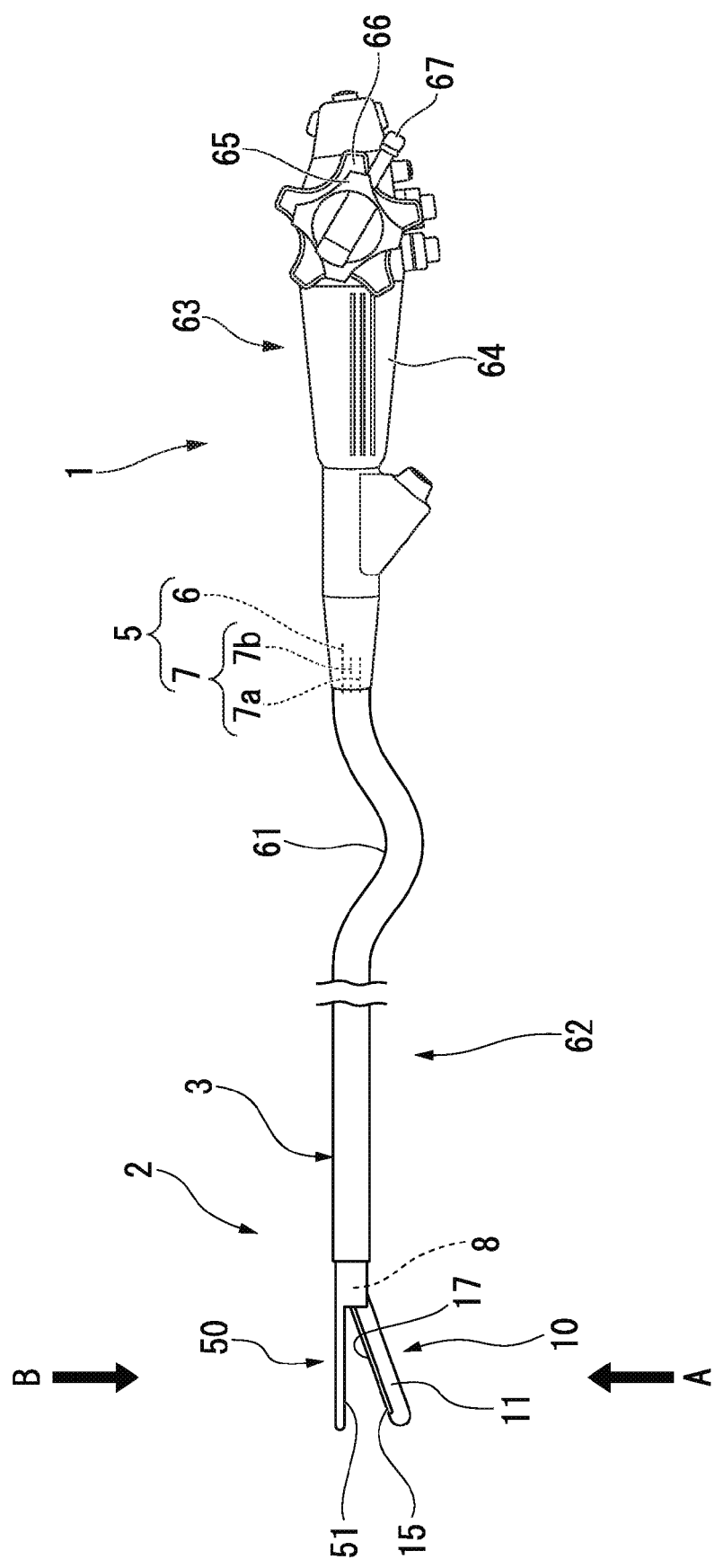
FIG. 1 is an overall view of a surgical instrument according to a first embodiment of the present invention.
Figure 2:
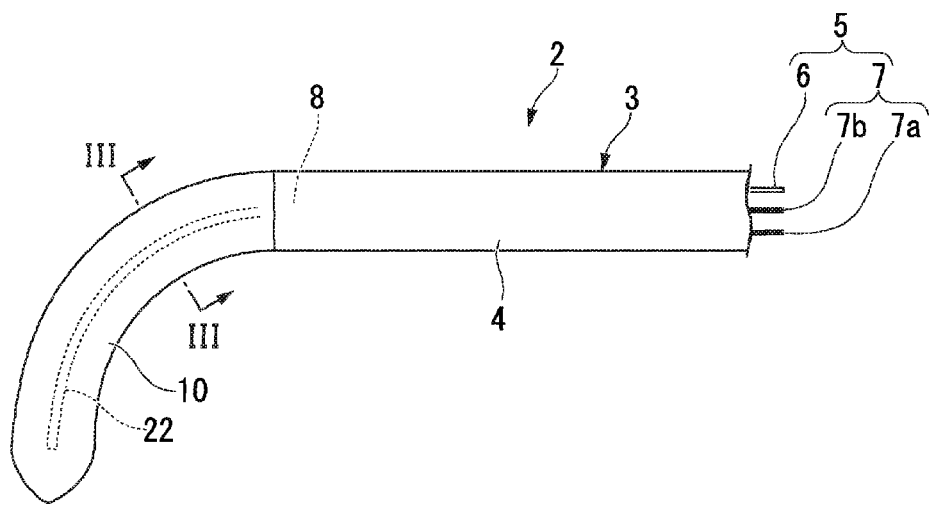
FIG. 2 is a schematic view showing a cartridge unit of the surgical instrument according to the first embodiment of the present invention.
Figure 3:
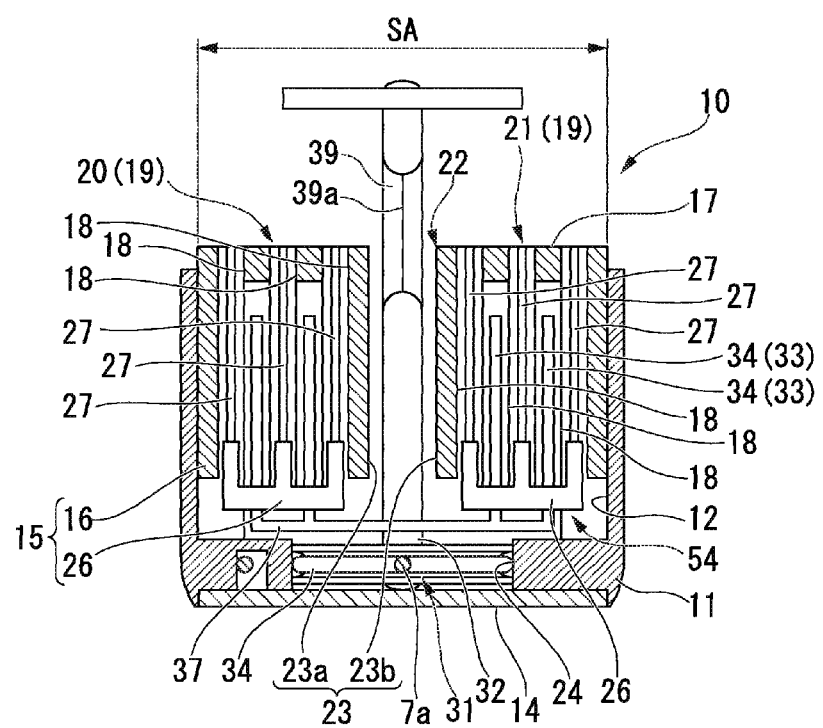
FIG. 3 is a cross-sectional view taken along line III-III of FIG. 2.
Figure 4:
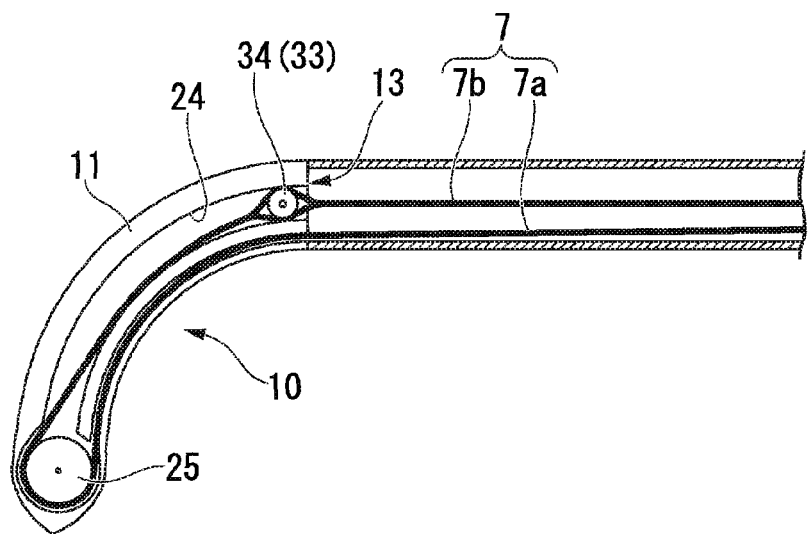
FIG. 4 is a partial cross-sectional view of the cartridge unit of the first embodiment of the present invention.
Figure 5:
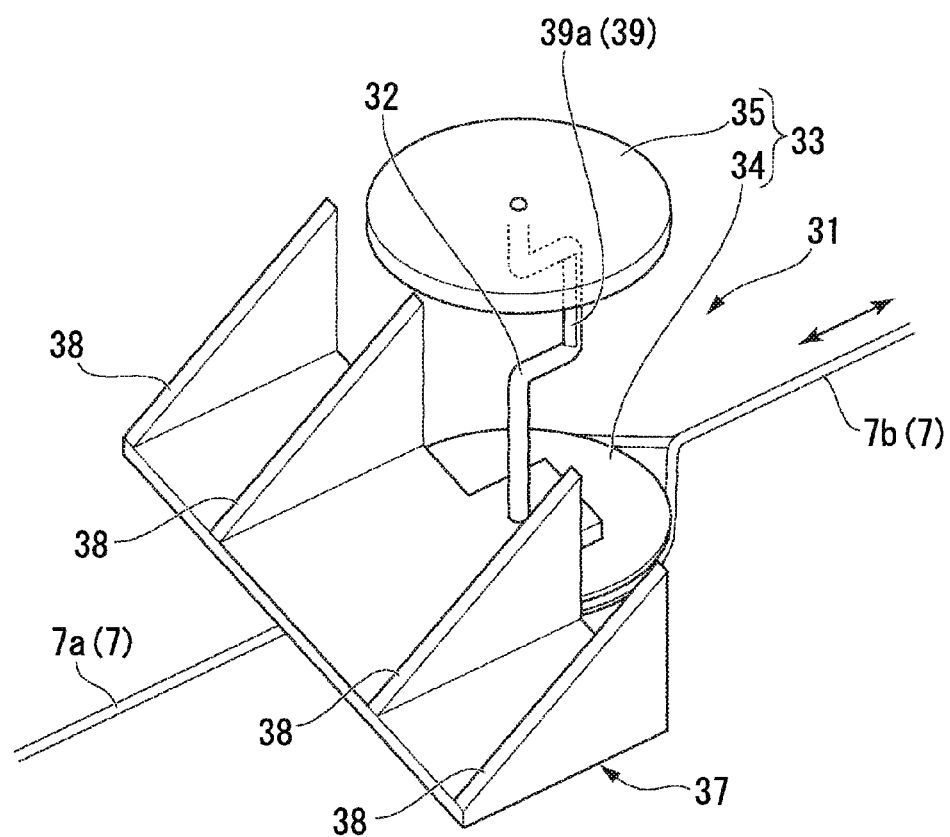
FIG. 5 is a perspective view showing an actuation section installed at the cartridge unit of the first embodiment of the present invention.
Figure 6:
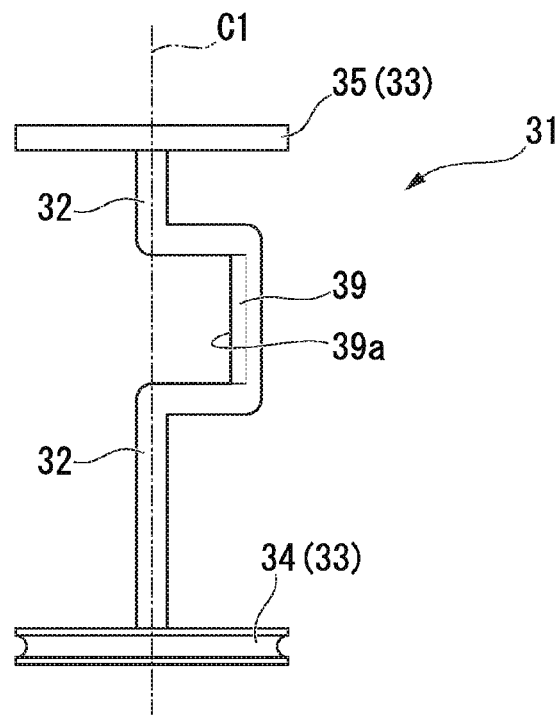
FIG. 6 is a side view of the actuation section of the first embodiment of the present invention.
Figure 7:
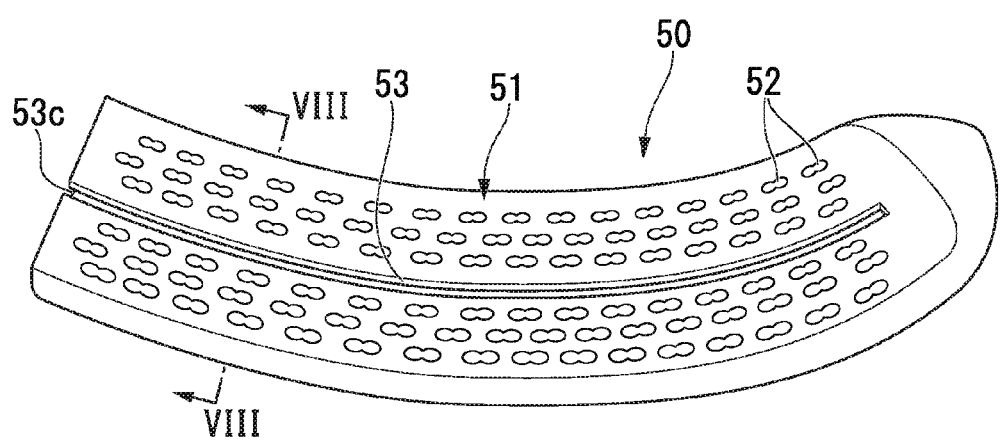
FIG. 7 is a perspective view showing a second jaw of the cartridge unit of the first embodiment of the present invention.
}
Figure 8:
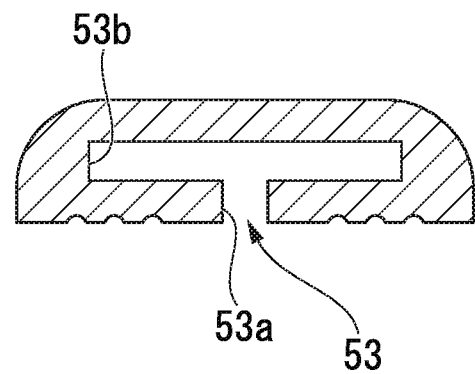
FIG. 8 is a cross-sectional view taken along line VIII-VIII of FIG. 7.

A first embodiment of the present invention will be described. FIG. 1 is an overall view of a surgical instrument 1 according to an embodiment. FIG. 2 is a schematic view showing a cartridge unit of the surgical instrument 1 seen in an arrow A direction shown in FIG. 1. FIG. 3 is a cross-sectional view taken along line III-III of FIG. 2. FIG. 4 is a partial cross-sectional view of the cartridge unit seen in an arrow B direction shown in FIG. 1. FIG. 5 is a perspective view showing an actuation section installed at the cartridge unit. FIG. 6 is a side view of the actuation section. FIG. 7 is a perspective view showing a second jaw of the cartridge unit. FIG. 8 is a cross-sectional view taken along line VIII-VIII of FIG. 7.

The surgical instrument 1 according to the embodiment shown in FIG. 1 is a medical tool configured to suture tissue using staples 27 (see FIG. 12) and to dissect the sutured area. The surgical instrument 1 includes an insertion section 62 which is capable of being inserted into a body, and a manipulation unit 63 connected to the insertion section 62. The insertion section 62 includes a cartridge unit 2 and a flexible tube 61. The cartridge unit 2 is filled with staples 27. A flexible tube 61 is connected to the cartridge unit 2.

The cartridge unit 2 has a root section 3, an open-close link section 8, a first jaw 10 and a second jaw 50.

As shown in FIGS. 1 and 2, the root section 3 is a substantially tubular area configured to connect the cartridge unit 2 to the flexible tube 61. A proximal end of the root section 3 is fixed to a distal end of the flexible tube 61. A distal end of the root section 3 is connected to the open-close link section 8 and the second jaw 50.

A connecting member 5 is inserted into the root section 3. The connecting member 5 is operated by manipulation of a user with respect to the manipulation unit 63.

The connecting member 5 has a first connecting member 6 and a second connecting member 7 (a wire). The first connecting member 6 is provided to open and close the first jaw 10 with respect to the second jaw 50. The second connecting member 7 is provided to operate an actuation section 31, which will be described below.

A proximal end of the first connecting member 6 extends to the manipulation unit 63. A distal end of the first connecting member 6 is connected to the open-close link section 8.

As shown in FIG. 4, the second connecting member 7 has a dissection connecting member 7a and a returning connecting member 7b. The dissection connecting member 7a is wound on a pulley section 25, which will be described below. The dissection connecting member 7a is inserted into a first guide section 24, which will be described below. A proximal end of the dissection connecting member 7a extends to the manipulation unit 63.

As shown in FIG. 5, a distal end of the returning connecting member 7b is connected to the actuation section 31. In the embodiment, the distal end of the returning connecting member 7b is connected to a proximal end of a shaft body 32, which will be described below. A proximal end of the returning connecting member 7b extends to the manipulation unit 63.

The open-close link section 8 is disposed at an inside of a distal portion of the root section 3 shown in FIG. 2. The open-close link section 8 has a link structure configured to convert movement of the first connecting member 6 in a center axis direction of the first connecting member 6 into open-close movement of the first jaw 10.

The first jaw 10 shown in FIGS. 2, 3 and 4 is provided at a distal end portion of the insertion section 62 (see FIG. 1) to grasp tissue. As shown in FIG. 2, the first jaw 10 has a predetermined curved shape. The first jaw 10 has a base section 11, a staple holder 15, the staples 27 and the actuation section 31.

As shown in FIG. 3, the base section 11 is a substantially rod-shaped or channel-shaped member having a longitudinal axis and a shape conforming to a curved shape of the first jaw 10. The base section 11 has a concave section 12, and a communication path 13 to the root section 3. The concave section 12 is capable of accommodating the staple holder 15 and the actuation section 31. The concave section 12 is opened toward a second grasping surface 51 of the second jaw 50. A bottom is formed at the concave section 12 by a cover 14. As shown in FIG. 4, the communication path 13 to the root section 3 is a passage through which the second connecting member 7 is inserted.

As shown in FIG. 3, the staple holder 15 has a holder main body 16, the pulley section 25 and a driver 26.

The holder main body 16 has a first grasping surface 17, an accommodating section 18 and a groove section 22. The first grasping surface 17 comes in contact with tissue when the tissue is grasped. The staples 27 are accommodated in the accommodating section 18. The groove section 22 is opened at the first grasping surface 17. The holder main body 16 is attached to the concave section 12 of the base section 11 in a direction in which the first grasping surface 17 is exposed from the base section 11.

The staple holder 15 is detachably attached to the base section 11. For example, after suture by using the staples 27, the staple holder 15 after use is capable of being removed from the base section 11. A suturation by using the surgical instrument 1 according to the embodiment is performed a plurality of times by attaching the staple holder 15 to the base section 11 in place of the used staple holders after suture by using the staples 27.

The first grasping surface 17 is a surface directed toward the second grasping surface 51 (see FIG. 1) of the second jaw 50 in a state in which the holder main body 16 is attached to the concave section 12 of the base section 11.

The staples 27 is capable of being accommodated in the accommodating section 18 in a state in which insertion ends of the staples 27 are directed toward the second grasping surface 51.

As shown in FIG. 3, in the first grasping surface 17, an inner region of an envelope curve that surrounds the plurality of accommodating sections 18 defines a suture area SA in which tissue is sutured by the staples 27. In a state in which the staples 27 are accommodated in the accommodating section 18, staple arrays 19 (a first staple array 20, a second staple array 21) are provided in two regions of the holder main body 16 divided by the groove section 22.

The first staple array 20 is constituted by the plurality of staples 27 arranged in an extending direction of the groove section 22. In the embodiment, the first staple array 20 is installed on the first grasping surface 17 in two or more rows at an interval.

The second staple array 21 is constituted by the plurality of staples 27 arranged in the extending direction of the groove section 22. In the embodiment, the second staple array 21 is installed on the first grasping surface 17 in two or more rows at an interval.

Accordingly, the staple array 19 has the plurality of staples 27, which is capable of being shot from the first jaw 10 toward the second jaw 50, around the groove section 22.

As shown in FIG. 3, the groove section 22 is a linear groove in which a blade section 39 (to be described below) of the actuation section 31 is accommodated to be capable of advancing and retracting. In the embodiment, the groove section 22 is formed in a curved shape. The groove section 22 defines a dissection line L (see FIGS. 9 and 12) in dissection of tissue.

The groove section 22 has a through-hole 23 and the first guide section 24. The through-hole 23 is opened at the first grasping surface 17. The first guide section 24 is continuous with the through-hole 23 and is formed in the holder main body 16.

The through-hole 23 has a first wall surface 23a and a second wall surface 23b that are apart from each other, and a bottom surface that connects the first wall surface 23a and the second wall surface 23b. In the embodiment, a bottom surface of the groove section 22 is constituted by a part of an inner surface of the base section 11. Further, in the embodiment, in an intermediate region of the first jaw 10 in the extending direction of the groove section 22, gaps between the first wall surface 23a and the bottom surface and between the second wall surface 23b and the bottom surface are formed at an intermediate region of the first jaw 10 in the extending direction of the groove section 22 for allowing the actuation section 31 to pass through the intermediate region.

As shown in FIG. 3, the first wall surface 23a has a surface crossing the first grasping surface 17 in the holder main body 16. The first wall surface 23a extends from the first grasping surface 17 of the holder main body 16 toward a bottom section of the concave section 12 of the base section 11. The first wall surface 23a extends in a longitudinal axis direction of the base section 11.

As shown in FIG. 3, the second wall surface 23b is a surface formed in parallel to the first wall surface 23a (including substantially in parallel) at a position apart from the first wall surface 23a by a distance at which the blade section 39 of the actuation section 31 is capable of passing therethrough. The second wall surface 23b is a surface crossing the first grasping surface 17 in the holder main body 16. The second wall surface 23b extends from the first grasping surface 17 of the holder main body 16 toward the bottom section of the concave section 12 of the base section 11. The second wall surface 23b extends in the longitudinal axis direction of the base section 11.

As shown in FIGS. 3 and 4, the first guide section 24 has a groove shape wider than an interval between the first wall surface 23a and the second wall surface 23b. The first guide section 24 extends to conform to a curved shape of the groove section 22. A first guided section 34 of a pair of guided sections 33 formed at the actuation section 31 is capable of coming in contact with the first guide section 24.

The dissection connecting member 7a is inserted into the first guide section 24. In the inside of the first guide section 24, the dissection connecting member 7a extends from a proximal end portion toward a distal end portion of the first guide section 24 along the first guide section 24, turns at the pulley section 25 of the distal end portion of the first guide section 24 to extend to the proximal end portion of the first guide section 24, and is connected to the actuation section 31. In the embodiment, a distal end of the dissection connecting member 7a is wound on an outer periphery of the first guided section 34, which will be described below.

The pulley section 25 shown in FIG. 4, on which the dissection connecting member 7a is wound, is rotatably connected to the base section 11.

The driver 26 shown in FIG. 3 is disposed in the accommodating section 18. The driver 26 is capable of being moved inside the accommodating section 18 by a cam section 37 of the actuation section 31. That is, when the driver 26 is moved toward an opening of the first grasping surface 17 side of the accommodating section 18 by the cam section 37 (see FIG. 5), the driver 26 pushes a connecting section 30 (see FIG. 12) of each of the staples 27 toward the opening of the first grasping surface 17 side to push out the staple 27 from the accommodating section 18.

The staple 27 has a pair of leg sections 28 and 29 (see FIG. 12) having insertion ends inserted into tissue, and the connecting section 30 that connects the pair of leg sections 28 and 29. The staple 27 is formed in a U shape (a U shape in which all angles are right angles) by bending deformable strands having high biocompatibility. A known structure may be selected and employed as the shape of the staple 27.

The actuation section 31 shown in FIGS. 3, 5 and 6 is disposed inside the base section 11. The actuation section 31 is configured to move the driver 26 to push out the staples 27 from the accommodating section 18 and also dissect the tissue after the staples 27 are pushed out.

As shown in FIGS. 3, 5 and 6, the actuation section 31 has the shaft body 32, the pair of guided sections 33, the cam section 37 and the blade section 39.

The shaft body 32 is connected to the distal end of the second connecting member 7 of the connecting member 5.

The shaft body 32 is capable of being guided and moved to a second guide section 53 (see FIG. 7) formed at the first guide section 24 and the second grasping surface 51, which will be described below, by moving the second connecting member 7 in a center axis direction of the second connecting member. A centerline C1 (see FIG. 6) of the shaft body 32 is a rotational center of the actuation section 31 in the embodiment. That is, in the embodiment, the actuation section 31 is rotatable within a predetermined range about the centerline C1 of the shaft body 32 serving as a rotational center while being supported by the first guide section 24 and the second guide section 53. The allowable range of rotation of the actuation section 31 in the embodiment is between a state in which the blade section 39 comes in contact with the first wall surface 23a and a state in which the blade section 39 comes in contact with the second wall surface 23b. The pair of guided sections 33, the cam section 37 and the blade section 39 are attached to the shaft body 32.

The pair of guided sections 33 are members engaged with the first guide section 24 and the second guide section 53. In the embodiment, the pair of guided sections 33 have the first guided section 34 engaged with the first guide section 24 and a second guided section 35 engaged with the second guide section 53.

The first guided section 34 is fixed to an end disposed at the first jaw 10 side, in both ends of the shaft body 32. The first guided section 34 has a disk shape having a centerline in a thickness direction of the first guided section. A groove to which a distal end of the dissection connecting member 7a is hooked is formed to extend in the circumferential direction at an outer periphery of the first guided section 34. A distal end portion of the dissection connecting member 7a is annularly hooked to the first guided section 34. The first guided section 34 is rotatable with respect to the distal portion of the dissection connecting member 7a. In the embodiment, a centerline of the first guided section 34 is coaxial with the centerline C1 of the shaft body 32. The first guided section 34 is rotatable in the first guide section 24 together with the shaft body 32. The first guided section 34 is attached to the shaft body 32 by a screw 34a. The first guided section 34 and the shaft body 32 may be integrally formed.

The second guided section 35 is fixed to an end disposed at the second jaw 50 side, in both ends of the shaft body 32. The second guided section 35 has a disk shape having a centerline in a thickness direction the second guided section. In the embodiment, the centerline of the second guided section 35 is coaxial with the centerline C1 of the shaft body 32. The second guided section 35 is rotatable in the second guide section 53 together with the shaft body 32. The second guided section 35 is attached to the shaft body 32 by a screw 35a. The second guided section 35 and the shaft body 32 may be integrally formed.

As shown in FIGS. 3 and 5, the cam section 37 is connected to the shaft body 32 to be rotatable with respect to the shaft body 32. The cam section 37 has an inclined surface 38 inclined with respect to a longitudinal axis of the base section 11. The inclined surface 38 of the cam section 37 comes in contact with the driver 26 to move the driver 26 when the cam section 37 is moved in the longitudinal axis direction of the base section 11. The moving direction of the cam section 37 is an extending direction of the groove section 22.

As shown in FIG. 6, the blade section 39 is disposed at a position apart from the shaft body 32 in a direction crossing the direction in which the centerline C1 of the shaft body 32 extends. The blade section 39 is connected to the shaft body 32 at a position between the ends of the shaft body 32. The blade section 39 has a blade edge 39a extending in parallel to the centerline C1 of the shaft body 32. The blade edge 39a has a sharp shape that is capable of dissecting tissue of a living body. As shown in FIG. 3, the blade section 39 is disposed at the groove section 22 so as to protrude from the first grasping surface 17 toward the second jaw 50. The blade section 39 is positioned closer to the proximal side than the cam section 37 when the blade section 39 is positioned closest to the groove section 22 by rotation of the actuation section 31, which will be described below.

The blade edge 39a is in a position apart from the centerline C1 of the shaft body 32 and directed toward the shaft body 32. For this reason, the blade section 39 is capable of dissecting tissue while being pressed to a proximal side in a dissection direction of the tissue by the blade section 39 by which the blade edge 39a comes in contact with the tissue of the living body. When the blade section 39 is pushed by the tissue of the living body, the blade section 39 is rotated about the centerline C1 of the shaft body 32 (serving as a rotational center of the actuation section 31 in the embodiment).

In the embodiment, when the first jaw 10 and the second jaw 50 are in a closed state, the blade edge 39a is formed in at least a gap portion between the first grasping surface 17 and the second grasping surface 51.

The second jaw 50 shown in FIGS. 1 and 7 is provides at a distal end portion of the insertion section 62 to grasp the tissue, and have a predetermined curved shape same as the first jaw 10. The second jaw 50 has the second grasping surface 51 in which a plurality of forming pockets 52 is formed.

The second grasping surface 51 is a surface directed toward the first grasping surface 17 of the first jaw 10. When the first jaw 10 is closed with respect to the second jaw 50, a distance between the first grasping surface 17 of the first jaw 10 and the second grasping surface 51 of the second jaw 50 is previously set according to a thickness of tissue serving as a suture target. The distance between the first grasping surface 17 of the first jaw 10 and the second grasping surface 51 of the second jaw 50 is set to a distance at which adhesion of the tissue serving as a suture target occurs after suture by using the staples 27 and excessive debridement of the tissue serving as the suture target is hard to occur.

The forming pockets 52 and the second guide section 53 are formed at the second grasping surface 51. The second guide section 53 is formed such that the second guided section 35 is capable of entering and to extend in the longitudinal axis direction of the second jaw 50.

Figure 12:
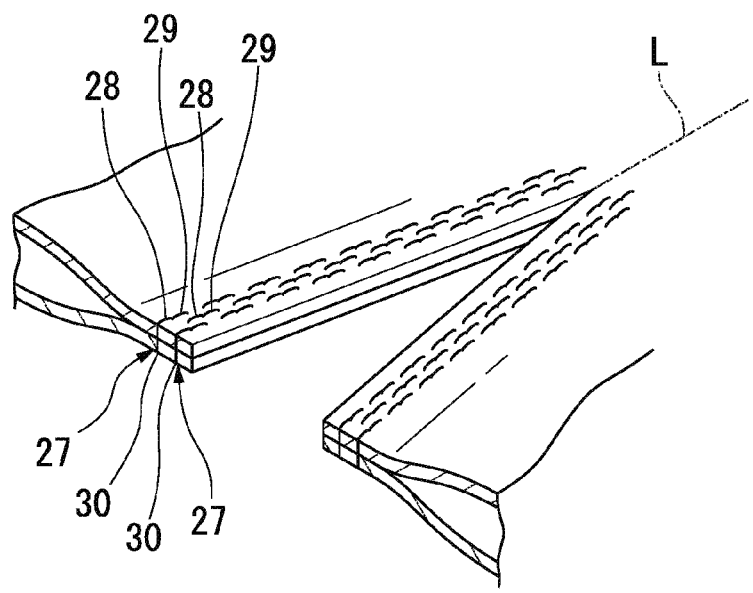
FIG. 12 is a view showing an action of the surgical instrument according to the first embodiment of the present invention.

Each of the forming pockets 52 shown in FIG. 7 has an inclined surface or a curved surface configured to guide the leg sections 28 and 29 to plastically deform the leg sections 28 and 29 of the staple 27 to form a shape in which the tissue is sutured as shown in FIG. 12.

As shown in FIG. 8, the second guide section 53 has an opening section 53a through which the shaft body 32 shown in FIG. 6 is capable of being inserted, and a groove section 53b wider than the opening section 53a and in which the second guided section 35 is slidable. As shown in FIG. 7, the second guide section 53 has a linear shape along a curved shape of the groove section 22 (see FIGS. 2 and 3). A shape of the groove section 53b is appropriately set according to the shape of the second guided section 35.

An inlet 53c configured to allow the second guided section 35 to enter the second guide section 53 is formed at a proximal portion of the second guide section 53. For this reason, when the actuation section 31 is positioned closest to the proximal side with respect to the groove section 22, the second guided section 35 is removed from the second guide section 53. Accordingly, when the actuation section 31 is positioned closest to the proximal side with respect to the groove section 22, the first jaw 10 and the second jaw 50 is capable of being freely opened and closed in a state in which they are not connected by the actuation section 31.

In the embodiment, a suture unit 54 in which the tissue is sutured (see FIG. 3) is constituted by the staple holder 15, the staples 27, the cam section 37 and the second jaw 50.

As shown in FIG. 1, the flexible tube 61 is a tubular elongated member. The connecting member 5 (the first connecting member 6, the dissection connecting member 7a and the returning connecting member 7b) is inserted through the flexible tube 61.

A proximal end of the root section 3 of the cartridge unit 2 is fixed to a distal end of the flexible tube 61. The proximal end of the flexible tube 61 is fixed to the manipulation unit 63.

In addition, a pipe line configured to guide a known observation apparatus (for example, an endoscope) for observing a suture area from the manipulation unit 63 toward the cartridge unit 2 may be installed at the flexible tube 61.

The manipulation unit 63 is provided at the proximal end of the flexible tube 61. The manipulation unit 63 is provided to allow a user to perform manipulation of opening and closing the first jaw 10 and the second jaw 50, to staple the staples 27 to the tissue, and to dissect the tissue. The manipulation unit 63 has substantially a rod shape such that an operator is capable of gripping the manipulation unit 63 with her or his hands.

The manipulation unit 63 has a housing 64, a curved knob 65, an open-close knob 66, a lever 67, and a transmission mechanism (not shown). The housing 64 has substantially a rod shape and is formed a space inside the housing The curved knob 65 is provided to bend the flexible tube 61. The open-close knob 66 and the lever 67 are disposed to be exposed to the outside of the housing 64 to operate the connecting member 5. The transmission mechanism is connected to the connecting member 5 in the housing 64.

The curved knob 65 is a member configured to bend the flexible tube 61 by pulling an angle wire (not shown) extending from the distal end of the flexible tube 61 to the manipulation unit 63. The curved knob 65 is rotatable with respect to the housing 64 of the manipulation unit 63, and is capable of being fixed not to be rotated with respect to the housing 64 at an arbitrary position.

The open-close knob 66 is a member configured to advance and retract the first connecting member 6 in the centerline direction. The open-close knob 66 is rotatable with respect to the housing 64 of the manipulation unit 63, and is capable of being fixed not to be rotated with respect to the housing 64 at an arbitrary position.

As an operator operates the open-close knob 66, the transmission mechanism (not shown) transmits an amount of manipulation of the open-close knob 66 to the first connecting member 6 as an amount of force to advance and retract the first connecting member 6 in the centerline direction.

The lever 67 is a member configured to advance and retract the second connecting member 7 in the centerline direction. The lever 67 is swingable with respect to the housing 64 of the manipulation unit 63, and in capable of being fixed not to be swung with respect to the housing 64 at an arbitrary position.

As the operator operates the lever 67, the transmission mechanism (not shown) transmits an amount of manipulation of the lever 67 to the second connecting member 7 as an amount of force to advance and retract the second connecting member 7 in the centerline direction. In the embodiment, the dissection connecting member 7a is pulled to the proximal side when the lever 67 is swung in a first predetermined direction, and the returning connecting member 7b is pulled to the proximal side when the lever 67 is swung in a direction opposite to the first predetermined direction.

In addition, the dissection connecting member 7a and the returning connecting member 7b are connected via the actuation section 31 in the cartridge unit 2. For this reason, the returning connecting member 7b is moved to the distal side when the dissection connecting member 7a is pulled to the proximal side by the lever 67, and the dissection connecting member 7a is moved to the distal side when the returning connecting member 7b is pulled to the proximal side by the lever 67.

Next, an action of the surgical instrument according to the embodiment will be described. FIGS. 9 to 12 are views showing the action of the surgical instrument 1 according to the embodiment.

As shown in FIG. 3, the surgical instrument 1 is prepared in a state in which the staples 27 are accommodated in the accommodating section 18 and the cam section 37 and the blade section 39 are disposed in the vicinity of the proximal end of the base section 11. At this time, the pair of guided sections 33 of the actuation section 31 are disposed in the vicinity of the proximal ends of the first guide section 24 and the second guide section 53.

The surgical instrument 1 is guided to a treatment target area through a natural opening of a patient such as the mouth or the like of the patient, a small incision portion formed in an abdominal wall or the like of the patient by a known technology.

Figure 9:
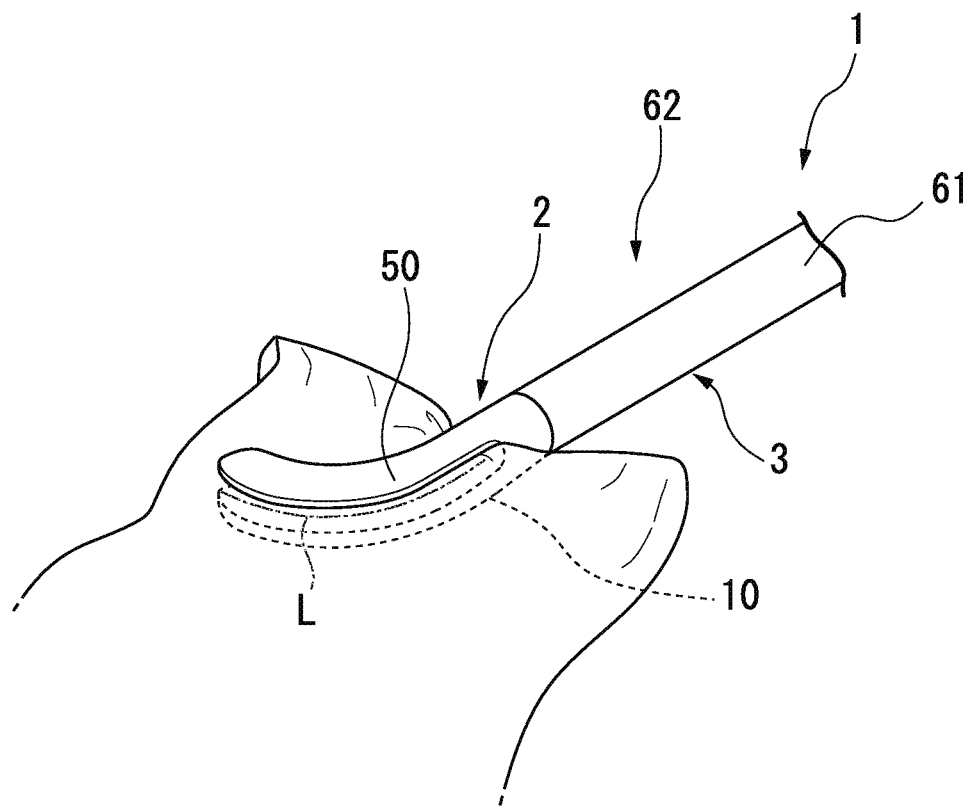
FIG. 9 is a view showing an action of the surgical instrument according to the first embodiment of the present invention.

As shown in FIG. 9, the first jaw 10 and the second jaw 50 provided at the distal end portion of the insertion section 62 of the surgical instrument 1 grasp the tissue serving as the dissection target in accordance with a manipulation of the open-close knob 66 (see FIG. 1) of the manipulation unit 63 under observation of a laparoscope (not shown).

As the tissue serving as the dissection target is grasped by the first jaw 10 and the second jaw 50 as shown in FIG. 9, the dissection line L with respect to the dissection target tissue is defined. As a user fixes the open-close knob 66 shown in FIG. 1 to the housing 64, as shown in FIG. 9, a position of the first jaw 10 with respect to the second jaw 50 is fixed in a state in which the first jaw 10 and the second jaw 50 grasp the tissue.

The user operates the lever 67 to move the dissection connecting member 7a to the proximal side after fixing the open-close knob 66 shown in FIG. 1 to the housing 64. The dissection connecting member 7a moved to the proximal side moves the actuation section 31 to the distal side as a pulling direction is reversed by the pulley section 25 shown in FIG. 4. The actuation section 31 moves both of the cam section 37 and the blade section 39 shown in FIGS. 3 and 5 to the distal side. The driver 26 shown in FIG. 3 is pushed up by the inclined surface 38 of the cam section 37 which is moved to the distal side. The driver 26 shown in FIG. 3 pushes out the staples 27 from the accommodating section 18 such that insertion ends of the staples 27 pierce into the tissue as the driver 26 is pushed up to the inclined surface 38 of the actuation section 31.

Further, when the staples 27 are pushed out from the accommodating section 18, the leg sections 28 and 29 of the staples 27 abut the forming pockets 52 (see FIG. 7). The forming pockets 52 deform the leg sections 28 and 29 of the staples 27 into a predetermined shape for suturing the tissue as shown in FIG. 12. The staples 27 are sequentially shot from the accommodating section 18 from the proximal side toward the distal side of the first jaw 10 in accordance with a movement of the cam section 37. In this way, the suture unit 54 shown in FIG. 3 sutures the tissue grasped by the first jaw 10 and the second jaw 50 via the staples 27.

Figure 10:
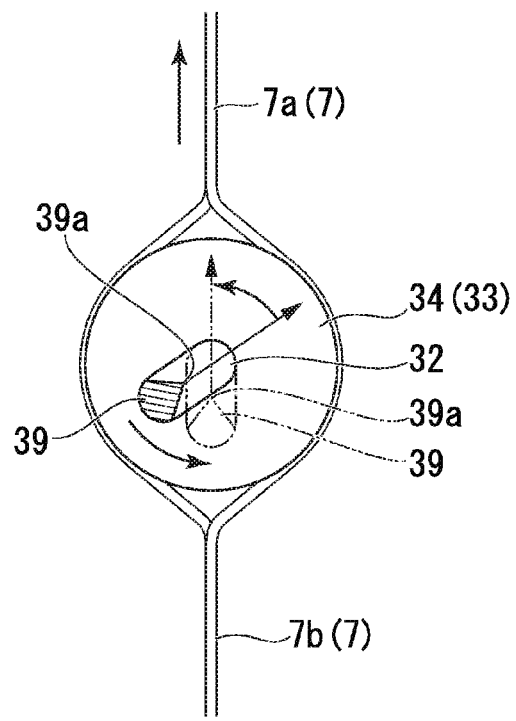
FIG. 10 is a view showing an action of the surgical instrument according to the first embodiment of the present invention.
Figure 11:
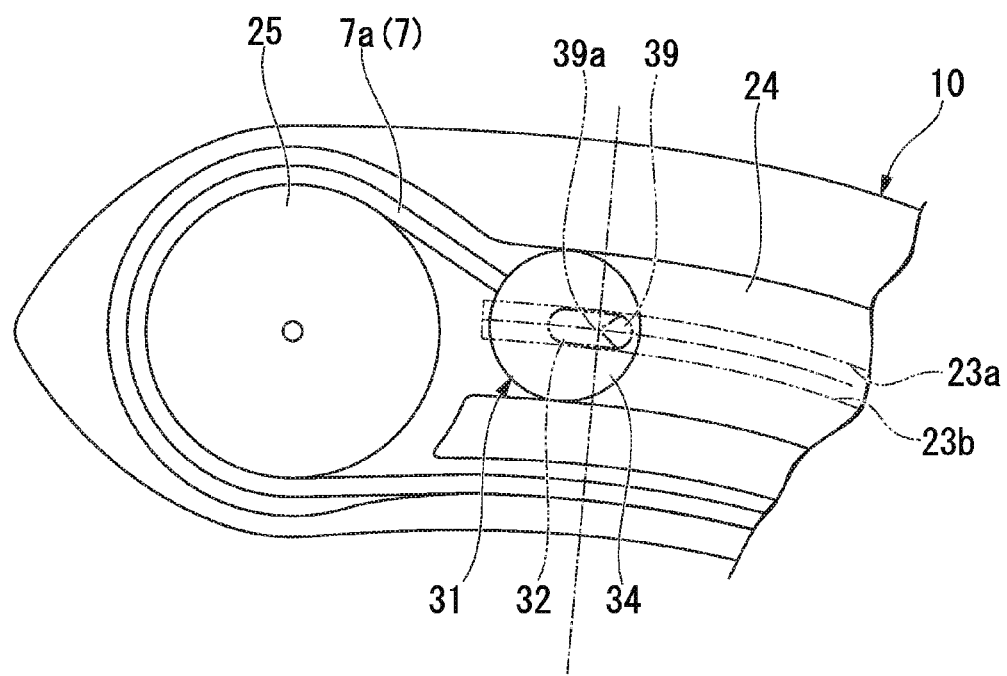
FIG. 11 is a view showing an action of the surgical instrument according to the first embodiment of the present invention.

The actuation section 31 is capable of being moved along the groove section 22 by the second connecting member 7. The blade section 39 (see FIGS. 5 and 6) disposed at the proximal side of the cam section 37 moves along the groove section 22 between the first staple array 20 and the second staple array 21 serving as the dissection line L (see FIGS. 9 and 12) as the blade section 39 is pulled by the dissection connecting member 7a. In a process in which the actuation section 31 is pulled by the dissection connecting member 7a and dissects the tissue of the living body, the blade edge 39a is pressed against the tissue, and the actuation section 31 rotates about a centerline of each of the pair of guided sections 33 serving as a rotational center. Here, as shown in FIGS. 10 and 11, the blade edge 39a of the blade section 39 comes in contact with neither the first wall surface 23a nor the second wall surface 23b of the groove section 22, the shaft body 32 rotates about the centerline of each of the pair of guided sections 33 serving as a rotational center due to rotation of the actuation section 31, and the blade section 39 rotates about the shaft body 32. The blade section 39 is moved to a hand side (a proximal side of the groove section 22) in a moving direction of the actuation section 31 by rotation of the blade section 39, and a direction of the blade edge 39a is a pulling direction of the actuation section 31 by the dissection connecting member 7a. That is, in a process in which the actuation section 31 is pulled by the dissection connecting member 7a to dissect the tissue, the blade edge 39a is directed in the pulling direction of the actuation section 31 by the dissection connecting member 7a. Here, the blade edge 39a is directed in a tangential direction of the curved groove section 22.

In a process in which the actuation section 31 is pulled by the dissection connecting member 7a, since the blade edge 39a is moved so as to be dragged by the shaft body 32 in a direction away from the first wall surface 23a or the second wall surface 23b shown in FIG. 3 the blade edge 39a is hard to bite into the first wall surface 23a or the second wall surface 23b.

The tissue is sequentially dissected by the blade section 39 from an area sutured by the staples 27. The blade section 39 dissects the tissue in the suture area SA, in the tissue grasped by the first jaw 10 and the second jaw 50.

After completion of suture by the staples 27 and dissection by the blade section 39, the user releases fixing of a lever 69 by a fixing section 70 and opens the first jaw 10 with respect to the second jaw 50. Accordingly, grasping of the tissue by the first jaw 10 and the second jaw 50 is released.

According to necessity, the actuation section 31 is capable of moving to the proximal end side of the groove section 22 by which the returning connecting member 7b is moved to the proximal side by operating the lever 67. When the actuation section 31 is positioned at the proximal end portion of the groove section 22, the empty staple holder 15 after shooting of the staples 27 is capable of replacing with a new staple holder 15.

When treatment is performed a plurality of times by using the surgical instrument 1 according to the embodiment, suture and dissection are capable of continuously performing by replacing the staple holder 15 with a new one after shooting the staples 27 to continue suture and dissection.

In the related art, in the tool for dissecting the tissue by biting into the tissue using the blade edge of the blade section by pushing the blade section for dissecitng the tissue of the living body, the blade section may unsteadily move when the tissue is pushed out from the proximal side of the blade section. In particular, when the blade section is pushed out along the curved dissection line, in order to prevent unsteadily moving of the blade section, a direction in which a compressive force is applied to the blade section should be adjusted in an advance direction of the blade section.

On the other hand, according to the surgical instrument 1 of the embodiment, since the blade edge 39a of the blade section 39 is directed toward the distal side of the groove section 22 in the tangential direction of the groove section 22 by which the actuation section 31 having the blade section 39 is pulled by the dissection connecting member 7a, unsteadily movement of the blade section 39 is hard to occur, movement of the blade section 39 is smoothly performed, and dissection of the tissue is stabilized.

(Second Embodiment)

Figure 13:
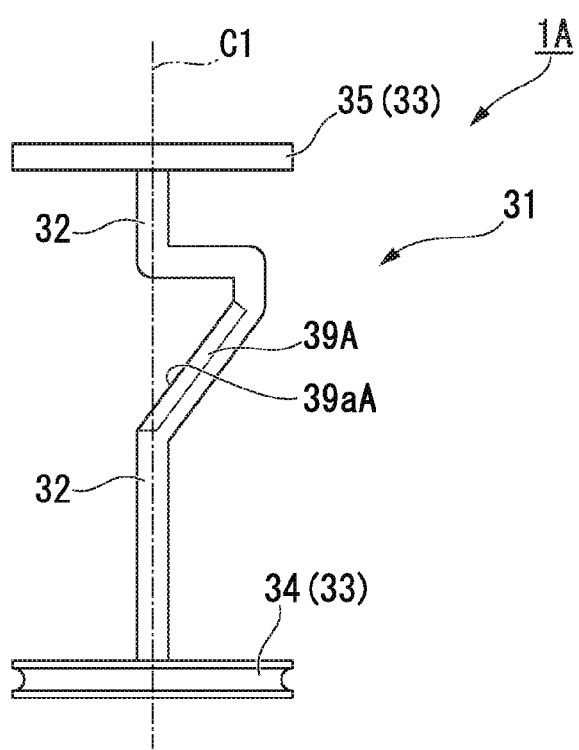
FIG. 13 is a side view showing an actuation section of a surgical instrument according to a second embodiment of the present invention.

Next, a second embodiment of the present invention will be described. In the embodiments described below, the same components as the components in description of the first embodiment are designated by the same reference numerals as in the first embodiment, and overlapping description will be omitted. FIG. 13 is a side view showing an actuation section of a surgical instrument 1A according to the embodiment.

As shown in FIG. 13, the surgical instrument 1A according to the embodiment is different from the first embodiment in that a blade section 39A has a blade edge 39aA extending to be inclined with respect to the centerline C1 of the shaft body 32.

The blade edge 39aA is formed along a straight line crossing the centerline C1 of the shaft body 32. In the blade edge 39aA, half or more of the entire length of the blade edge 39aA is directed toward the centerline C1 of the shaft body 32.

In the embodiment, the blade edge 39aA extends in a direction inclined with respect to an advance direction of the blade edge 39aA. For this reason, the tissue of the living body is capable of being dissected with a force smaller than that of the blade edge 39a described in the first embodiment.

(Third Embodiment)

Figure 14:
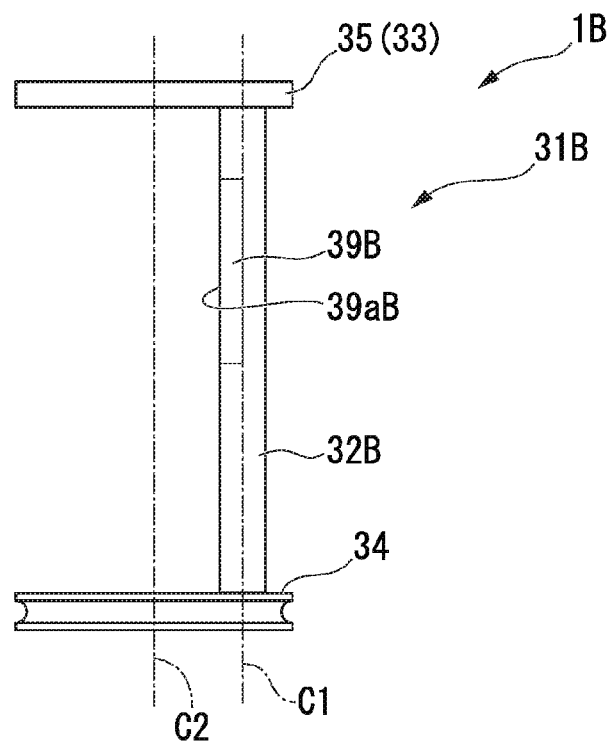
FIG. 14 is a side view showing an actuation section of a surgical instrument according to a third embodiment of the present invention.

Next, a third embodiment of the present invention will be described. FIG. 14 is a side view showing an actuation section of a surgical instrument 1B according to the embodiment.

As shown in FIG. 14, in the surgical instrument 1B according to the embodiment, an actuation section 31B having a different configuration different from the actuation section 31 described in the first embodiment is provided instead of the actuation section 31 described in the first embodiment.

The actuation section 31B is different from the first embodiment in that a shaft body 32B is fixed to a position offset with respect to a centerline of each of the pair of guided sections 33, instead of the shaft body 32 described in the first embodiment.

In the embodiment, the actuation section 31B rotates about a centerline C2 of each of the pair of guided sections 33. The shaft body 32B rotates about the centerline C2 each of the pair of guided sections 33 serving as a rotational center due to rotation of the actuation section 31B about the centerline C2 of each of the pair of guided sections 33 serving as a rotational center.

A blade section 39B configured to dissect the tissue of the living body like the first embodiment is provided at the shaft body 32B. The blade section 39B has a blade edge 39aB directed to a centerline of each of the pair of guided sections 33 extending parallel to a centerline of each of the pair of guided sections 33.

In this embodiment as well, the actuation section 31B is movable along the groove section 22 by the second connecting member 7. In a process in which the actuation section 31B is pulled by the dissection connecting member 7a and dissects the tissue of the living body, the tissue pushes the blade edge 39aB like the first embodiment, and the actuation section 31B rotates about the center line of each of the pair of guided sections 33 serving as a rotational center. Then, the shaft body 32B rotates about a centerline of each of the pair of guided sections 33, and the blade section 39B rotates about a centerline of each of the pair of guided sections 33. The blade section 39 moves to a hand side in the moving direction of the actuation section 31B (a proximal side of the groove section 22).

In a process in which the actuation section 31B is pulled by the dissection connecting member 7a and dissects the tissue, the blade edge 39aB is directed in a pulling direction of the actuation section 31B by the dissection connecting member 7a. At this time, the blade edge 39aB is directed in a tangential direction of the curved groove section 22.

Accordingly, in this embodiment, like the first embodiment, since the blade section 39B is guided by the first guide section 24 and the second guide section 53 while being held with no contact with the groove section 22, movement of the blade section 39B in a dissection process of the tissue is smooth.

(Fourth Embodiment)

Figure 15:
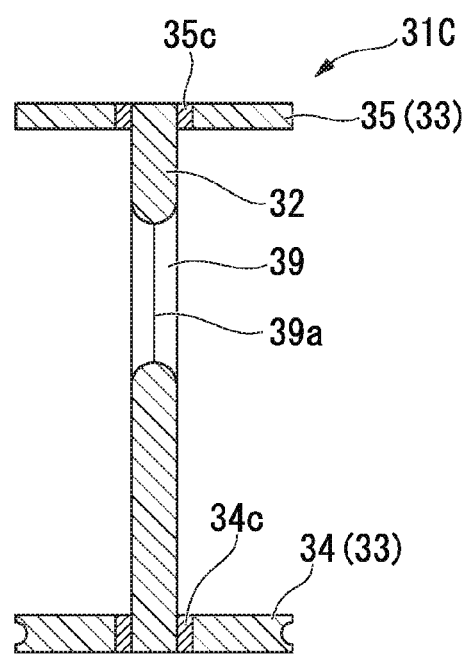
FIG. 15 is a side view showing an actuation section of a surgical instrument according to a fourth embodiment of the present invention.

Next, a fourth embodiment of the present invention will be described. FIG. 15 is a cross-sectional view showing an actuation section 31C of a surgical instrument according to the embodiment.

As shown in FIG. 15, in the embodiment, the actuation section 31C having a different configuration from the actuation section 31 described in the first embodiment is provided instead of the actuation section 31 described in the first embodiment.

The actuation section 31C is different from the first embodiment in that the shaft body 32 is connected to the pair of guided sections 33 such that the shaft body 32 is rotatable with respect to the pair of guided sections 33.

That is, in the embodiment, a bearing 34c interposed between the first guided section 34 and the shaft body 32 and a bearing 35c interposed between the second guided section 35 and the shaft body 32 are provided.

In the embodiment, in addition to rotation of the actuation section 31C as a whole, the blade section 39 is rotatable when the shaft body 32 is rotated with respect to the first guided section 34 and the second guided section 35 as well. In the embodiment, the blade section 39 is rotatable with a force smaller than that in the first embodiment.

(Fifth Embodiment)

Figure 16:
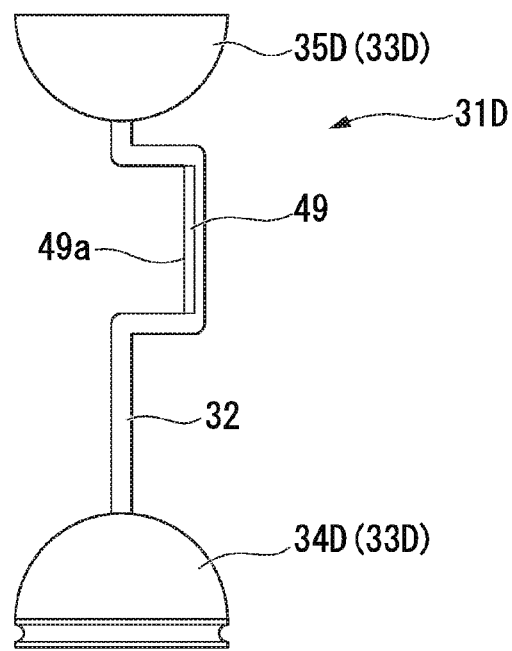
FIG. 16 is a side view showing an actuation section of a surgical instrument according to a fifth embodiment of the present invention.
Figure 17:
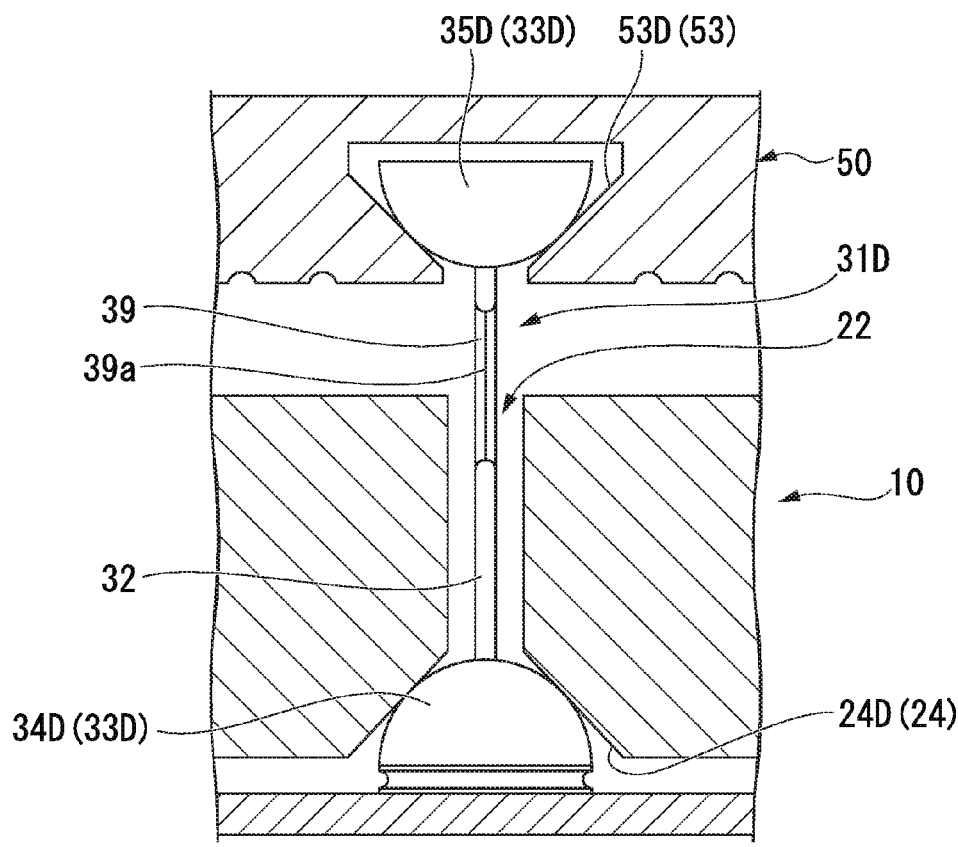
FIG. 17 is a cross-sectional view showing configurations of a first guide section and a second guide section of the surgical instrument according to the fifth embodiment of the present invention, and showing the same cross section as taken along line III-III of FIG. 2.

Next, a fifth embodiment of the present invention will be described. FIG. 16 is a side view showing an actuation section 31D of a surgical instrument according to the embodiment. FIG. 17 is a cross-sectional view showing configurations of the first guide section 24 and the second guide section 53 of the surgical instrument according to the embodiment, and showing the same cross section taken along line III-III of FIG. 2.

As shown in FIGS. 16 and 17, in the embodiment, the actuation section 31D having a different configuration from the actuation section 31 described in the first embodiment is provided instead of the actuation section 31 described in the first embodiment.

The actuation section 31D has a pair of guided sections 33D (a first guided section 34D, a second guided section 35D) of which a surface directed to the shaft body 32 forms a curved surface, instead of the pair of guided sections 33 of the first embodiment.

In the first guided section 34D, the surface directed toward the shaft body 32 is formed in a curved surface protruding toward the shaft body 32 (a hemispherical shape in the embodiment), and the surface directed toward the shaft body 32 is a sliding surface that comes in point contact with the first guide section 24.

In the second guided section 35D, the surface directed toward the shaft body 32 is formed in a curved surface shape protruding toward the shaft body 32 (a hemispherical shape in the embodiment), and the surface directed toward the shaft body 32 is a sliding surface in point contact with the second guide section 53.

In addition, in the embodiment, the first guide section 24 and the second guide section 53 have inclined surfaces 24D and 53D that are inclined in a V shape respectively. The first guided section 34D and the second guided section 35D come in point contact with the inclined surface 24D and the inclined surface 53D.

Even when a rotational center of the actuation section 31D is inclined, the first guided section 34D or the second guided section 35D respectively comes in point contact with the first guide section 24 or the second guide section 53. For this reason, in comparison with the actuation section 31 of the first embodiment, in the actuation section 31D including the pair of guided sections 33D of the embodiment, sliding resistance when the actuation section 31D is pulled in a state in which a rotational center is inclined is reduced, and the tissue of the living body is capable of being dissected with a small force.

(Sixth Embodiment)

Figure 18:
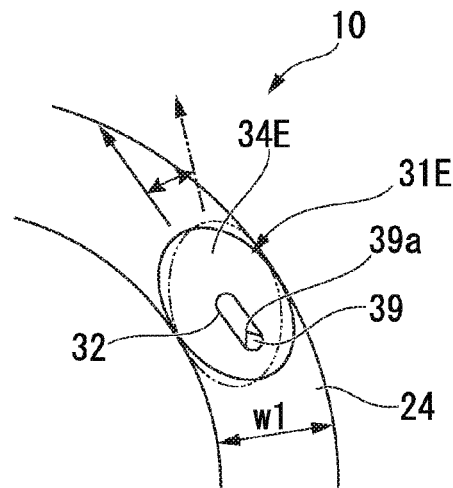
FIG. 18 is a schematic view showing an actuation section and a first guide section of a surgical instrument according to a sixth embodiment of the present invention.

Next, a sixth embodiment of the present invention will be described. FIG. 18 is a schematic view showing an actuation section 31E and a first guide section 24 of a surgical instrument according to the embodiment.

As shown in FIG. 18, in the embodiment, the actuation section 31E having a different configuration from the actuation section 31 described in the first embodiment is provided instead of the actuation section 31 described in the first embodiment.

The actuation section 31E has a first guided section 34E having an elliptical disk shape, instead of the first guided section 34 of the first embodiment.

The first guided section 34E has a longitudinal axis larger than a width wl of the first guide section 24 and a short axis slightly smaller than the width w 1 of the first guide section 24.

In the embodiment, the actuation section 31E is assembled upon assembly of the first jaw 10 such that the blade section 39 is disposed closer to a proximal side than the shaft body 32 when the first guided section 34E enters the first guide section 24. For this reason, a rotatable range of the actuation section 31E is limited to a range in which the first guided section 34E is rotatable in the first guide section 24. A stopper structure constituted by the first guided section 34E abuts onto the first guide section 24 to restrict that the shaft body 32 rotates 180° or more with respect to the first guide section 24.

In the embodiment, movement of the blade section 39 to the distal side farther than the shaft body 32 is prevented by the first guided section 34E. For this reason, the blade edge 39a of the blade section 39 is always substantially directed toward the distal side. For this reason, when the actuation section 31E is pulled using the dissection connecting member 7a, it is prevented that the tissue is not dissected as a result from abutting a side of the blade section 39 opposite to the blade edge 39a with the tissue.

In the embodiment, a second guided section (not shown) having an elliptical disk shape may be provided instead of the second guided section 35 of the first embodiment.

(Seventh Embodiment)

Figure 19:
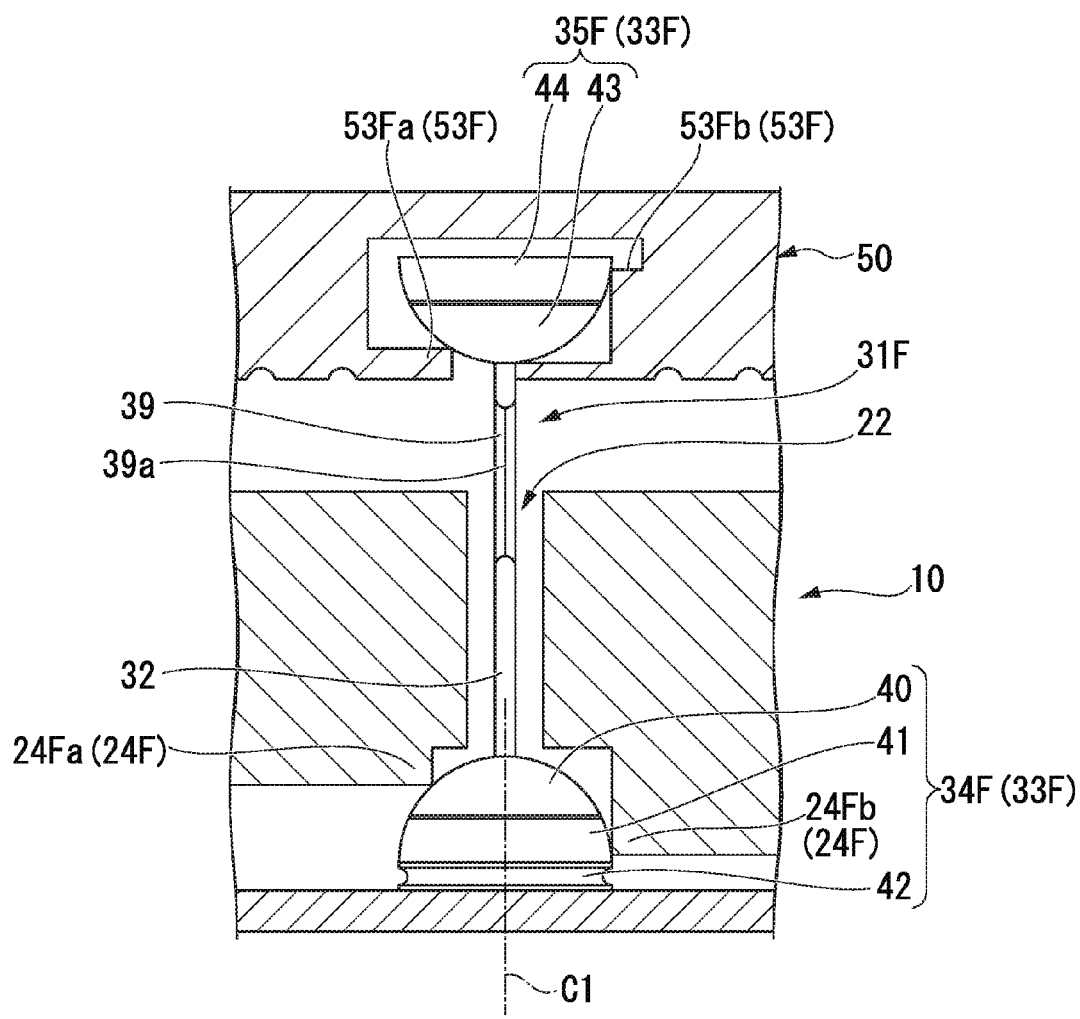
FIG. 19 is a cross-sectional view showing configurations of an actuation section, a first guide section and a second guide section of a surgical instrument according to a seventh embodiment of the present invention, and showing the same cross section as taken along line III-III of FIG. 2.

Next, a seventh embodiment of the present invention will be described. FIG. 19 is a cross-sectional view showing configurations of an actuation section 31F, a first guide section 24F and a second guide section 53F of a surgical instrument according to the embodiment, and showing the same cross section taken along line III-III of FIG. 2.

As shown in FIG. 10, in the embodiment, the first guide section 24F and the second guide section 53F having different configurations from the first guide section 24 and the second guide section 53 described in the first embodiment are provided instead of the first guide section 24 and the second guide section 53 described in the first embodiment. In addition, in the embodiment, the actuation section 31F having a different configuration from the actuation section 31 described in the first embodiment is provided instead of the actuation section 31 described in the first embodiment.

The first guide section 24F has a wall section 24Fa and a wall section 24Fb having different heights at an inner periphery side and an outer periphery side of the curved shape of the groove section 22.

The second guide section 53F has a wall section 53Fa and a wall section 53Fb having different heights at an inner periphery side and an outer periphery side of the curved shape of the groove section 22.

The actuation section 31F has a pair of guided sections 33F constituted by a first guided section 34F and a second guided section 35F, instead of the pair of guided sections 33 described in the first embodiment.

The first guided section 34F has a first inner rotation member 40 rotatable with respect to the shaft body 32, a first outer rotation member 41 coaxial with the first inner rotation member 40 and connected to the first inner rotation member 40, and a pulley plate 42 connected to the dissection connecting member 7a like the first embodiment.

The first inner rotation member 40 and the first outer rotation member 41 are relatively rotatable about the centerline C1 of the shaft body 32 serving as a rotational center.

The first inner rotation member 40 is capable of abutting the wall section 24Fa at the inner periphery side of the curved shape of the groove section 22, in the wall section 24Fa and the wall section 24Fb.

The first outer rotation member 41 is capable of abutting the wall section 24Fb at the outer periphery side of the curved shape of the groove section 22, in the wall section 24Fa and the wall section 24Fb.

The second guided section 35F has a second inner rotation member 43 that is rotatable with respect to the shaft body 32, and a second outer rotation member 44 coaxial with the second inner rotation member 43 and connected to the second inner rotation member 43.

The second inner rotation member 43 and the second outer rotation member 44 are relatively rotatable about the centerline C1 of the shaft body 32 serving as a rotational center.

The second inner rotation member 43 is capable of abutting the wall section 53Fa at the inner periphery side of the curved shape of the groove section 22, in the wall section 53Fa and the wall section 53Fb.

The second outer rotation member 44 is capable of abutting the wall section 53Fb at the outer periphery side of the curved shape of the groove section 22, in the wall section 53Fa and the wall section 53Fb.

In the embodiment, when the actuation section 31F is guided by the first guide section 24F and the second guide section 53F, the first inner rotation member 40 and the first outer rotation member 41 is capable of being rotated in opposite directions, and the second inner rotation member 43 and the second outer rotation member 44 is capable of being rotated in opposite directions.

For this reason, the pair of guided sections 33F are rolled with respect to the first guide section 24F and the second guide section 53F, and a resistance at this time is rolling friction smaller than sliding friction. As a result, the actuation section 31F and the blade section 39 thereof smoothly advance along the groove section 22.

While embodiments of the present invention have been described in detail above with reference to the accompanying drawings, the specific configurations are not limited to the embodiment but may include design changes without departing from the spirit of the present invention.

For example, while the flexible surgical instrument 1 including the flexible tube 61 has been exemplarily described in the embodiments, a hard shaft may be provided instead of the flexible tube 61.

While an example in which the first jaw 10 and the second jaw 50 are opened and closed by using the open-close knob 66 has been described in the above-mentioned embodiments, the jaws may be configured such that an open-close operation in the cartridge unit 2 and dissection of the tissue by the blade section 39 of the actuation section 31 are performed as one operation. For example, when the actuation section 31 is moved to the distal side of the cartridge unit 2 by using the lever 67, the actuation section 31 may be configured to connect the first jaw 10 and the second jaw 50 to move the first jaw 10 toward the second jaw 50. In this case, the open-close operation in the cartridge unit 2 and dissection of the tissue by the blade section 39 of the actuation section 31 may be performed as one operation using the lever 67.

While embodiments of the present invention have been described above, the technical scope of the present invention is not limited to the embodiments, but combination of the components in the embodiments can be varied, and various modifications of the components can be added or deleted without departing from the spirit of the present invention. The present invention is not limited to the above-mentioned description.

What is claimed is:

1. A surgical instrument comprising:
   an insertion section configured to be inserted into a body;
   a first jaw and a second jaw provided at a distal end portion of the insertion section, the first jaw and the second jaw having predetermined curved shapes and configured to grasp tissue;
   a guide section formed along the predetermined curved shape and disposed in at least one of the first jaw and the second jaw;
   an actuation section which is movable by being guided by the guide section;
   a shaft body provided at the actuation section and in which a center line of the shaft body extends from the first jaw toward the second jaw, the shaft body configured to be rotatable about a rotation axis that is the same as or parallel to the center line; and a blade section which is connected to the shaft body at a position apart from the rotation axis and which is arranged to face the rotation axis, the blade section being rotatable with respect to the first jaw and the second jaw about the rotation axis.

2. The surgical instrument according to claim 1, further comprising a wire extending from a proximal end portion to a distal end portion of the guide section, the wire turning at the distal end portion of the guide section to extend back toward the proximal end portion of the guide section, the wire being connected to the actuation section.

3. The surgical instrument according to claim 2, wherein
the actuation section has a guided section having a disk-shape, the guided section being engaged with the guide section and in which the wire is wound on an outer periphery of the guided section, and the shaft body is fixed to the guided section such that the center line of the shaft body passes through a center of the guided section.

4. The surgical instrument according to claim 3, wherein the guided section has a sliding surface which forms a curved surface shape protruding toward the shaft body at a surface to which the shaft body is fixed among outer surfaces of the guided section, the sliding surface which comes in point contact with the guide section.

5. The surgical instrument according to claim 2, wherein the blade section is inclined with respect to the center line of the shaft body.

6. The surgical instrument according to claim 2, wherein
the actuation section has a guided section formed in a disk-shape, the guided section being engaged with the guide section and in which the wire is wound on an outer periphery of the guided section, and the shaft body is fixed to the guided section such that the center line of the shaft body extends in parallel to a center line of the guided section at a position apart from a center of the guided section.

7. The surgical instrument according to claim 2, wherein
the actuation section has a guided section formed in a disk-shape, the guided section being engaged with the guide section and in which the wire is wound on an outer periphery of the guided section, and the shaft body is connected to the guided section such that the center line of the shaft body passes through a center of the guided section and the shaft body is rotatable with respect to the guided section.

8. The surgical instrument according to claim 2, wherein the actuation section has a stopper structure which is capable of abutting the guide section to restrict the shaft body from rotating 180° or more with respect to the guide section.

9. The surgical instrument according to claim 1, further comprising a suture unit configured to suture the tissue grasped by the first jaw and the second jaw.

10. A tissue dissecting unit comprising:
an actuation section which is movable along a predetermined curved shape of a jaw having the predetermined curved shape;

a shaft body provided at the actuation section; and a blade section connected to the shaft body, wherein the shaft body and the blade section are rotatable with respect to the actuation section about a rotation axis that is the same as or parallel to a center line of the shaft body, and the blade section is disposed at a position apart from the rotation axis, and connected to the shaft body so as to face the rotation axis.

* * * * *